US00PP33875P2

(12) United States Plant Patent
Hansen

(10) Patent No.: US PP33,875 P2
(45) Date of Patent: Jan. 18, 2022

(54) ***CLEMATIS* PLANT NAMED 'RAIN DANCE'**

(50) Latin Name: ***Clematis* hybrid**
Varietal Denomination: Rain Dance

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/300,648

(22) Filed: Sep. 8, 2021

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
See application file for complete search history.

*Primary Examiner* — Susan McCormick Ewoldt

(57) ABSTRACT

The new hybrid plant of *Clematis* 'Rain Dance' of compact, medium height, upright, non-vining habit with combined ovate and trifoliate leaves and dark purple buds producing nodding flowers with typically four reflexed tepals of indigo-blue beginning late May and reblooming through late summer.

1 Drawing Sheet

Botanical denomination: *Clematis* hybrid.
Cultivar designation: 'Rain Dance'.

STATEMENT REGARDING PRIOR DISCLOSURES UNDER 37 CFR 1.77(B)(6)

The first public disclosure of the claimed plant, in the form of a sale, was made by Walters Gardens, Inc. Oct. 5, 2020 to Hoover's Greenhouse, Farmer Bailey and Vermont Wildflower Farm. No plants were in condition to sell prior to Oct. 5, 2020. Prior to that, on Feb. 1, 2020 the claimed plant was displayed with a non-enabling photograph and brief description in a website operated by Walters Gardens, Inc., and on May 21, 2020 as a non-enabling photograph and brief description in the 2020-2021 Catalog by Walters Gardens, Inc., who obtained the plant and all information relating thereto, from the inventor. No plants of *Clematis* 'Rain Dance' were in condition to sell prior to the first sale, nor have been sold, in this country or anywhere in the world, nor has any disclosure of the new plant been made more than one year prior the filing date of this application, and such sale or disclosure within one year was either derived directly or indirectly from the inventor.

BACKGROUND OF THE INVENTION

The present invention relates to a new and distinct plant of herbaceous type *Clematis*. The new plant is the result of a single seedling selection from a cross between an unnamed, proprietary selection of a *Clematis fremontii* x *Clematis integrifolia* cross (not patented) as the female parent times 'Ashva' (not patented). The cross was performed on Jun. 16, 2014 by the inventor at a wholesale perennial nursery in Zeeland, Mich., USA. The new plant passed the original evaluation in summer of 2016 at the same nursery in Zeeland, Mich., and was the assigned the breeder code 14-5-1 during these remaining trials. The new plant was selected from among many other seedlings growing at the same nursery in Zeeland, Mich. which met the rigorous criteria of excellent flowers, foliage and habit established as breeding goals.

'Rain Dance' has been asexually propagated since 2016 by shoot tip cuttings at the same nursery in Zeeland, Mich. The resultant asexually propagated plants have remained stable and exhibit the identical characteristics as the original plant in multiple generations.

BRIEF SUMMARY OF THE INVENTION

'Rain Dance' differs from all other *Clematis* known to the applicant. The nearest known cultivars are *Clematis* 'Center Star' U.S. Plant Pat. No. 17,010, 'Cleminov 51' U.S. Plant Pat. No. 17,012, 'Stand by Me' U.S. Plant Pat. No. 30,556, 'Violet Stardust' U.S. Plant Pat. No. 30,555, *Clematis* x *durandii* (not patented) 'Stand by Me Lavender' copending U.S. Plant Patent Application.

'Center Star' is shorter than the new plant, the flowers are flatter and more upright, with typically five tepals that are less recurved and more purple-blue in color. 'Cleminov 51' is shorter in habit and has darker colored violet-purple flowers, more recurved tepals. 'Violet Stardust' has a similar habit and the smaller flowers are more violet-blue. The x *durandii* forms are not as tall and not as floriferous. 'Stand by Me' has a shorter habit with foliage having a more purplish-bronze cast to the back of the foliage when young and more bell-shaped flowers with violet-blue tepals. 'Stand by Me Lavender' has a shorter habit with more dusty lavender flowers.

The new plant is taller than the female parent, more floriferous and more vigorous than both the female and male parents and the flowers are more bell-shaped. 'Ashva' is has a taller, vining, woody habit, and the flowers are larger with broader ruffled tepals typically of five to six that are violet purple on the margins with a reddish purple center bar.

The new plant, 'Rain Dance', differs from all *Clematis* known to the inventor in the following combined traits:

1. The foliage is both ovate and trifoliate, and micro-tomentose below and glabrous above;
2. Outwardly-facing flowers begin in early spring to June with rebloom in the late summer typically having four tepals per flower;
3. Large outwardly-facing flowers of indigo-blue tepals develop;
4. Plant habit is intermediate in height, benefits from stakes or other nearby plants when mature.

BRIEF DESCRIPTION OF THE DRAWINGS

The photographs of the new plant demonstrate the overall appearance of trial garden at a wholesale perennial nursery in Zeeland, Mich., USA. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
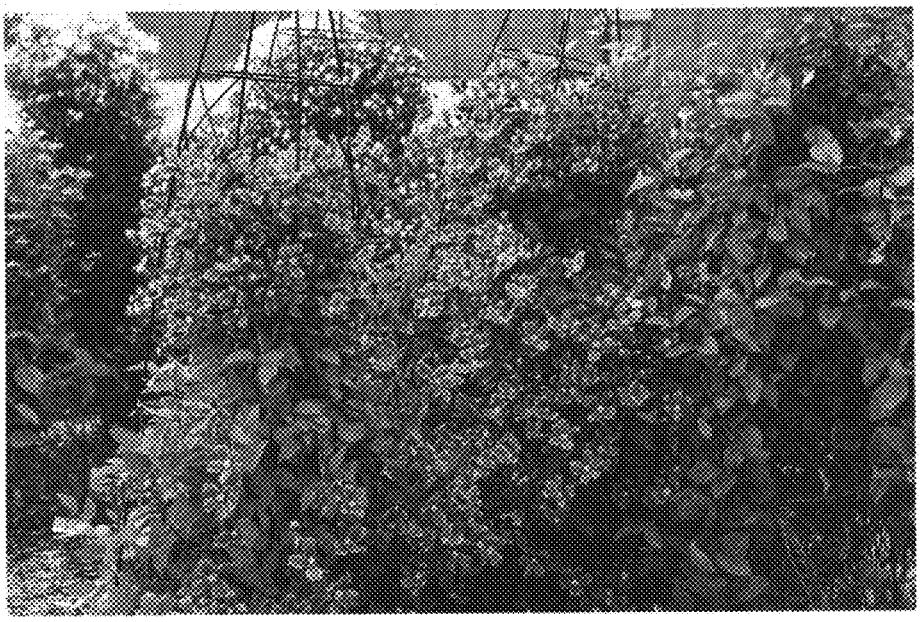
FIG. 1 shows two five-year-old plants in peak flower supported by a trellis.
Figure 2:
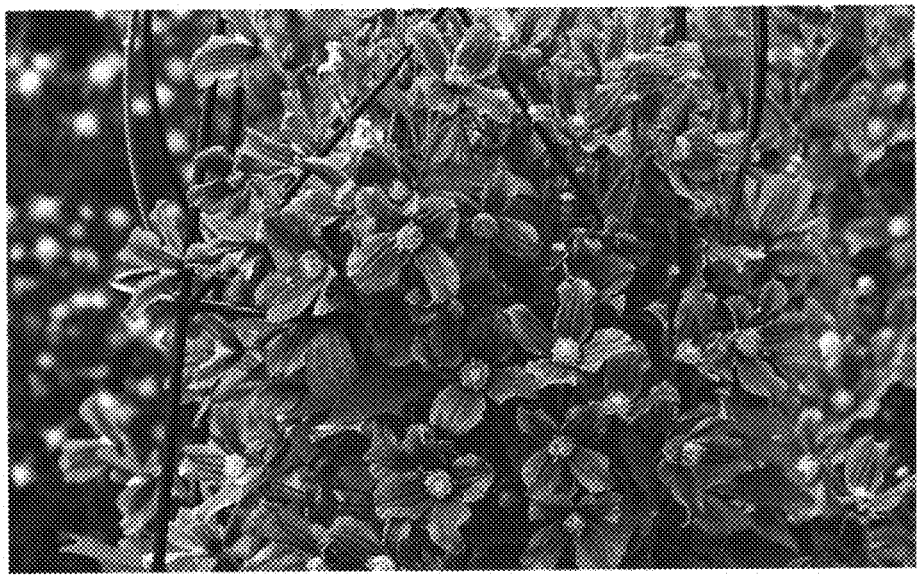
FIG. 2 a close-up of the flowers from above early in the season on a five-year-old plant.

The following description is based on a five-year-old plant growing in a full-sun trial garden with supplemental water and fertilizer at a wholesale perennial nursery in Zeeland, Mich., USA. The new plant has not been grown under all possible environments and may phenotypically appear different under different conditions such as light, temperatures, fertilizer, and water, without any difference in genotype. The color descriptions are from the 2015 edition of The Royal Horticultural Society Colour Chart except where common dictionary terms are used.

Parentage: The female (seed parent) is a proprietary unnamed hybrid of *fremontii* x *integrifolia*; the male (pollen parent) is 'Ashva';

Plant habit: Winter-hardy, herbaceous perennial of semi-woody stems producing upright habit, dying to the ground each winter; to about 155.0 cm tall in flower and spreading to about 102.0 cm across about 40.0 cm above soil; foliage to about 152.0 cm tall;

Roots: Coarse; branched; tan to light brown in color depending on soil type;

Growth rate: Rapid, finishing in four-liter container in about 8 to 10 weeks from a one-year-old vernalized plant;

Stems: To about 48 per plant; cylindrical with longitudinal carina; glabrous proximally and micro-puberulent distally; branched in upper nodes; to about 152.0 cm long and 7.0 mm diameter at base; flowering in upper one-third to one-half of plant;

Stem color: Older proximal stems nearest RHS N200D with carina nearest RHS N187A, younger proximal stems between RHS 178A and RHS 177B; distal stems nearest RHS 146D with carina nearest RHS N186C;

Branches: Erect, parallel main stem; with longitudinal carina; glabrous proximally, micro-puberulent distally; to about 30 cm long and 2.5 mm diameter at base;

Branch color: Nearest RHS 146D with carina nearest RHS N186C;

Internode: About 15 to 17 per stems to 8.0 mm across;

Internode color: Variable, proximally nearest N186A, distally nearest RHS N186A on older stems, nearest RHS 145A on young stems in lower light and nearest RHS 187B on young stems in high light exposure;

Foliage: Opposite; variable, simple and trifoliate; ovate and ovate lobed; leaves and lobes apex acute, base oblique, margin entire, minutely tomentose abaxial and glabrate adaxial; newly expanded foliage is upright, maturing to flat and horizontal;

Leaf blade size: Variable; simple — to about 8.0 cm long and 5.7 cm wide near base; trifoliate — to about 11.5 cm long and about 8.0 cm wide in middle with side lobes to 6.6 cm long and 3.3 cm wide and center lobe to 7.7 cm long and 4.7 cm wide;

Leaf color: Proximal mature leaves adaxial surface nearest RHS 137A, abaxial surface nearest RHS 147B; young emerging leaves adaxial surface nearest RHS 146C, abaxial surface nearest RHS 146C;

Petiole: Concavo-convex; glabrous; size variable, to 4.8 cm long and 3.5 mm wide at base for either simple or trifoliate, average about 2.2 cm long and 3.0 mm wide;

Petiole color: Young adaxial nearest RHS 146D with moderate blush of nearest RHS 183B, abaxial between RHS N144A and RHS 146D; mature adaxial nearest RHS 146D and abaxial nearest RHS 146D;

Rachis: Slightly concavo-convex; glabrous; to about 4.0 cm long and 1.5 mm diameter;

Rachis color: Adaxial and abaxial between RHS N144A and RHS 146D;

Petiolule: Slightly concavo-convex; glabrous; to about 4.0 mm long and 1.5 mm diameter;

Petiolule color: Adaxial and abaxial between RHS N144A and RHS 146D;

Veins: Palmate-penta-nerved to multi-costate; convergent; glabrous adaxial, micro-tomentose abaxial;

Vein color: Adaxial mature leaves between RHS 146B and RHS 146C; abaxial mature leaves in nearest RHS 146C; adaxial young leaves in nearest RHS 146D; abaxial young leaves nearest 146D;

Inflorescence: Flowers solitary; at nodes; flowering portion in distal one-half to one-third of the plant;

Flower attitude: Buds upright, flowers outwardly;

Flower fragrance: None detected;

Flower period: Late May to June with rebloom into late summer; individual flowers remaining effective in flower for about 6 to 8 days;

Peduncle: Cylindrical; micro-puberulent; to about 5.1 cm long and 2.0 mm in diameter, average 3.4 cm long and 1.5 mm diameter;

Peduncle attitude: Upright;

Peduncle color: Nearest RHS 146D with moderate blushing concentrated on carina nearest RHS 187A distally;

Buds one day prior to opening: Conical with narrowly acute apex, and rounded base; glabrous with carina along tepal unions tomentose; about 19.0 mm long and 11.0 mm diameter;

Bud color: Basal one-third between RHS 94B and RHS 94A transitioning to nearest RHS N88C at apex; carina between RHS 94B and RHS 94A nearly to apex;

Flower: Solitary; perfect; incomplete; campanulate, cruciform; actinomorphic; about 4.0 cm across at tepal apices and 1.8 cm deep;

Flower attitude: Outwardly;

Tepals: Typically four, occasionally five or six; lanceolate; broadly acute, apiculate, recurved apex; truncate base; tri- to penta-nerved with midrib and one or two pair of main veins, deeply furrowed in three main veins; margins entire proximally, distal one-half of margin erosulate; adaxial glabrous and matte; micro-puberulent abaxial between outer main vein and margin, glabrous and matte between outer two main veins and midrib; about 26.0 mm long and 16.0 mm wide in middle; self-cleaning;

Tepal color: Young and mature adaxial nearest RHS 94B outside of main veins and between RHS 94A and RHS 93B inside outer main veins, basal 1.0 mm portion nearest RHS NN155D; abaxial mature between RHS 92C and RHS 97C with basal 2.0 mm nearest RHS 96D, and veins nearest RHS 96A proximally and distal veins nearest RHS 92B; young abaxial nearest RHS 94D with basal 2.0 mm nearest RHS 97A, proximal veins nearest RHS 94A and distally becoming nearest RHS 94C;

Petals and sepals: Not present;

Androecium: About 60; flattened dorsa-ventrally, abaxial pubescent distal half, glabrous proximal half; total 12.0 mm long and 1.5 mm wide;

*Filaments*.—Flattened; pubescent abaxial, glabrous adaxial, margin ciliate; about 8.5 mm long and 1.5 mm wide and about 0.2 mm thick; color in distal one-half nearest RHS NN155B adaxial and abaxial, proximal one-half nearest RHS 92C.

*Anthers*.—Basifixed; longitudinal; ellipsoidal; puberulent abaxial; introrse; to about 3.5 mm long and 1.0 mm diameter, decreasing toward flower axis; color nearest RHS 165B.

*Pollen*.—Abundant; powdery; color nearest RHS 11D.

Gynoecium: About 70 to 80 internal to androecium; to 10.0 mm long;

*Style*.—Terete to tapered; about 7.0 mm long and 0.8 mm diameter; pilose to sericeous; color nearest RHS 138B covered in silvery hairs.

*Stigma*.—Cylindrical; about 3.0 mm long and 0.5 mm diameter; color nearest RHS 155C.

*Torus*.—Semi-dome shaped; about 4.0 mm diameter across at base and 3.0 mm tall; color nearest RHS 157A when young and nearest RHS N199B at maturity.

Reproductive structures:

*Fruit*.—Produced in globose plumose head, to about 4.2 cm diameter and 3.8 cm tall; seeds with plumose tails curved around equal distance above and below torus.

*Seed*.—Rare; flattened achene with style persistent as plumose tail; hairs adpressed becoming antrorse as maturing and at nearly 90 degree angle to style when mature, extending about 4.0 mm long; tail portion to 30.0 mm long; pubescent achene base 6.0 mm long, 5.0 mm wide and 1.0 mm thick.

*Seed color as developing*.—Plumose feather tail variable nearest RHS 189D and RHS N87A with hairs nearest RHS 198D, achene base center nearest RHS 146B and outside margins between RHS 146D and RHS 145A.

*Seed color when mature*.—Plumose feather tail nearest RHS N199B with hairs nearest RHS 164C, achene base some between RHS 165B and RHS 165A.

Culture: *Clematis* 'Rain Dance' grows best in full sun with ample moisture, good drainage and mulch. The new plant is cold hardy from USDA zones 3 to at least zone 8.

Disease and pest tolerance: Pest and disease resistance and tolerance outside of that normal for *Clematis* is not known at this time.

It is claimed:

1. The new and distinct ornamental plant named *Clematis* 'Rain Dance' as herein described and illustrated.

* * * * *